(12) United States Patent
Miyake et al.

(10) Patent No.: US 6,513,361 B2
(45) Date of Patent: Feb. 4, 2003

(54) METHOD FOR DETECTING LOW MOLECULAR WEIGHT COMPOUND IN SOLUTION

(75) Inventors: Jun Miyake, Ibaraki (JP); Chikashi Nakamura, Ibaraki (JP); Seong-Hun Song, Pusan (KR); Sang-Mok Chang, Pusan (KR); Takaaki Arai, Saitama (JP)

(73) Assignee: National Institute of Advanced Industrial Science and Technology (JP)

( * ) Notice: Subject to any disclaimer, the term of this patent is extended or adjusted under 35 U.S.C. 154(b) by 0 days.

(21) Appl. No.: 09/749,979

(22) Filed: Dec. 27, 2000

(65) Prior Publication Data

US 2002/0023493 A1 Feb. 28, 2002

(30) Foreign Application Priority Data

Aug. 30, 2000 (JP) ........................................ 2000-261373

(51) Int. Cl.⁷ .............................................. G01N 29/02
(52) U.S. Cl. ..................... 73/24.06; 73/61.49; 436/501; 422/68.1
(58) Field of Search .............................. 73/61.45, 61.49, 73/61.79, 61.75, 61.61, 64.53, 64.54, 64.42, 53.01, 24.01, 24.06, 579; 436/501; 422/68.1

(56) References Cited

U.S. PATENT DOCUMENTS

| 3,744,296 | A | * | 7/1973 | Beltzer | 73/23 |
| 5,179,028 | A | * | 1/1993 | Vali et al. | 436/524 |
| 5,552,274 | A | * | 9/1996 | Oyama et al. | 436/501 |
| 5,853,994 | A | * | 12/1998 | Gopinathan et al. | 73/61.41 |
| 5,866,798 | A | * | 2/1999 | Schonfeld et al. | 73/61.49 |
| 6,289,717 | B1 | * | 9/2001 | Thundat et al. | 73/24.06 |
| 6,295,861 | B1 | * | 10/2001 | Tom et al. | 73/24.06 |
| 6,339,954 | B1 | * | 1/2002 | Naganawa et al. | 3/61.79 |

OTHER PUBLICATIONS

Kawakami et al., "A selection of short peptides that interact with a porphyrin as a small target by immobilized phage display," *Chem. Commun.* (17) 1765–1766 [1999].

* cited by examiner

*Primary Examiner*—Helen Kwok
(74) *Attorney, Agent, or Firm*—Medlen & Carroll, LLP

(57) ABSTRACT

The invention relates to a method for detecting a low molecular weight compound in a solution which utilizes a quartz resonator and which comprises capturing a low molecular weight compound between an adsorptive film (A) for a low molecular weight compound provided on the surface of a quartz resonator and an adsorptive film (A) for a low molecular weight compound provided on the surface of a signal enhancing material and comprises detecting the shift in frequency of the quartz resonator before and after the capture.

7 Claims, 3 Drawing Sheets

METHOD FOR DETECTING LOW MOLECULAR WEIGHT COMPOUND IN SOLUTION

BACKGROUND OF THE INVENTION

The present invention relates to a method for detecting a low molecular weight compound by utilizing a quartz resonator, more particularly a method for detecting a low molecular weight compound in a solution with high sensitivity by utilizing a quartz resonator.

Generally, a quartz resonator analyzing apparatus comprising a quartz resonator, oscillating circuit and frequency measuring device is applied for the analyses of various substances in solutions, because the change in mass of a substance to be detected which is adsorbed on the surface of the quartz resonator is precisely grasped as the shift in the oscillating frequency. In recent years, there have appeared many proposals for more speedily detecting the change in mass and concentration of a substance to be detected by fixating, on the surface of a quartz resonator, various adsorptive films having adsorptivity for a substance to be detected.

These methods, however, are mostly ones for high molecular weight proteins that utilize antigen-antibody reaction or ones that make use of latex coagulation reaction, and at present there has been proposed no detection method effective for a low molecular weight compound in a solution, for example, porphyrin.

OBJECTS AND SUMMARY OF THE INVENTION

The present invention, which has been accomplished under the above circumstances, is aimed at providing a method for detecting a low molecular weight compound in a solution with high sensitivity.

The inventors found that, when an adsorptive film (A) for a low molecular weight compound is formed on the surface of a quartz resonator and such a film (A) is also formed on the surface of a signal enhancing material and when a solution of a low molecular weight compound is introduced in this measuring system, the low molecular weight compound is captured sandwich-wise efficiently between these films (A), and thus the inventors accomplished the present invention.

Namely, according to the present invention, the following inventions are provided.
(1) A method for detecting a low molecular weight compound in a solution which utilizes a quartz resonator and which comprises capturing a low molecular weight compound between an adsorptive film (A) for a low molecular weight compound provided on the surface of a quartz resonator and an adsorptive film (A) for a low molecular weight compound provided on the surface of a signal enhancing material and comprises detecting the shift in frequency of the quartz resonator before and after the capture.
(2) A detection method according to the above (1), wherein one molecule of a low molecular weight compound to be detected is combined to plural molecules of a material for forming the adsorptive film.
(3) A detection method according to the above (1) or (2), wherein the material for forming the adsorptive film (A) for a low molecular weight compound is a peptide.
(4) A detection method according to the above (3), wherein the peptide is an oligopeptide.
(5) A detection method according to the above (4), wherein the oligopeptide is one obtained by a combinatorial chemical technique.
(6) A detection method according to any one of the above (1) to (5), wherein the signal enhancing material is synthetic resin beads.
(7) A detection method according to the above (6), wherein the synthetic resin beads are polystyrene type beads.

The detection method of the present invention is explained concretely hereinafter.

[Quartz Resonator]

The quartz resonator used in the present invention is preferably one comparatively inexpensive with a frequency of about 5 to 10 MHz, since, although the higher its basic frequency the greater the response for oscillating frequency, such a high frequency type causes noises to increase, frequency stability to become lower and the unit price of the resonator to rise.

For a quartz resonator to be oscillated stably in a solution of a signal enhancing material, if only one side of the quartz resonator is made to touch to the solution, this suffices for it. And, for example, a technique is adopted wherein one side of the quartz resonator is affixed with a quartz piece using a silicone adhesive or covered with a silicone material.

As electrode materials for the quartz resonator, silver or gold is preferable. From the viewpoint of the magnitude of frequency response and the cheapness of price, silver is favorable. But from the viewpoint of the high level of frequency stability in solution and the resistance against oxidation of the electrode surface during preservation in the air before use, gold is more favorable.

[Low Molecular Weight Compound to be Detected]

As the low molecular weight compounds to be detected according to the present invention there are enumerated those that can combine with plural film forming materials in a monomolecular state, namely, low molecular weight organic compounds having symmetric structures, such as porphyrin, dioxin, PCB and the like.

These low molecular weight compounds are usually used in the form of being dissolved or dispersed in solvents, but preferably used in the form of solutions.

As the solvents, any can be employed as long as it dissolves or disperses the low molecular weight compounds. Such solvents include water and organic solvents such as alcohols and DMSO. A solvent having low polarity is usable, and, in that case, covering one side of the electrode, which has been mentioned above, is unnecessary.

[Formation of Adsorptive Film (A) for Low Molecular Weight Compound on Surface of Quartz Resonator]

In the present invention, there is provided, on the electrode surface of a quartz resonator, a film (A) having adsorptivity for a low molecular weight compound to be detected.

The film (A) may be any material as long as it has adsorptivity for the low molecular weight compound.

Materials for forming such a film include those which does not differ significantly in terms of molecular weight from low molecular weight compounds such as peptide, DNA and the like. The film forming material preferably used in the present invention is peptides.

As the method of forming the film, all the hither to known methods can be used such as dip coat method, spin coat method, casting method, LB method, self-assembled monolayer film forming method and the like.

The above-mentioned film (A) is preferably formed so that it may be oriented uniformly on the whole surface of the quartz resonator. However, the film is not necessarily formed uniformly on the surface if it can adsorb the low molecular weight compound of detection target and can pinch/capture the low molecular weight compound in cooperation with the film (A) provided on the latex beads (signal enhancing material) mentioned hereinafter.

The surface of the electrode of the quartz resonator sometimes has contaminants stuck thereon, and upon forming the film it is desirable to clean beforehand the surface of the quartz resonator with a suitable means, for example, with a peroxide solution.

[Formation of Adsorptive Film (A) for Low Molecular Weight Compound on Surface of Signal Enhancing Material]

In the present invention, on the surface of a signal enhancing material the adsorptive film (A) for low molecular weight compound is provided.

As the signal enhancing material, any of the heretofore known carriers can be used, such as synthetic resin beads, proteins, liposomes and gold colloids, as long as it has a large mass and allows the film (A) to be formed on its surface.

Among these, the synthetic resin beads can be put to reuse by a simple washing operation and are preferably used in the present invention.

As the synthetic resin beads there are enumerated beads formed from various resins and copolymer resins such as polystyrene type resin, polybutadiene type resin, polyethylene type resin, polypropylene type resin, polyisobutylene type resin, poly (acrylic acid) type resin, poly (methacrylic acid) type resin, poly (methyl methacrylate) type resin, poly(ethyl methacrylate) type resin, poly(propyl methacrylate) type resin, polyacrylamide type resin, poly (vinyl alcohol) type resin, poly (vinyl chloride) type resin, poly(vinylidene chloride) type resin, poly(maleic anhydride) type resin, poly(vinylidene fluoride) type resin, polyacrylonitrile type resin, poly (vinyl acetate) typeresinandpoly (ethyleneterephthalate) typeresin.

The materials for forming the film (A) on the surface of the signal enhancing material may be the same as those mentioned in the paragraph explaining the formation of the film (A) on the surface of the quartz resonator.

It is preferable that the signal enhancing material has a size not to cause gravitational sedimentation within a measuring time with its particle diameter being approximately 200 to 500 nm and that it can maintain a monodisperse state with its surface density of charge being −0.274 to −0.451 C/m$^2$.

Forming the film (A) on the surface of the signal enhancing material, for example, latex beads is preferably carried out by treating the surface beforehand for modification so as to make it easily combinable with the forming material of the film (A) and then by fixating the film (A).

As such treating methods for modification, for example in the case of a polystyrene copolymerized with acrylamide, a method may be adopted wherein fixation is performed by a crosslinking agent such as NHS by utilization of the carboxyl group presented by the acrylamide modification.

The above-mentioned film (A) is desirably formed uniformly on the whole of the surface of the signal enhancing material. However, it is not necessarily formed uniformly on the surface if it can adsorb the low molecular weight organic compound of detection target and can pinch/capture the low molecular weight organic compound in cooperation with the film (A) provided on the quartz resonator.

[Scheme of Detection Process of the Present Invention]

An outline of a typical process of the present invention is explained based on FIGS. 1 to 2 by taking an example wherein the substance to be detected is porphyrin and a peptide is used as the material for forming a thin film (A) for adsorption of the porphyrin.

In FIG. 2, in the measuring vessel (cell), there is fixed vertically the quartz resonator shown in FIG. 1, the electrode surface of which is provided with a peptide thin film. Further, in the measuring vessel, there are introduced the latex beads shown in FIG. 1 whose surfaces are provided with the peptide thin films. When porphyrin is put into this measuring vessel (cell), the porphyrin, as shown in FIG. 1, is bound and captured in a sandwich manner between the peptide thin film provided on the quartz resonator and the peptide thin films provided on the latex beads. For this reason, together with the porphyrin, a much larger mass of the latex beads compared with the porphyrin is adsorbed on the quartz resonator. An increase in signal due to this large mass links to a significant decrease in signal of the oscillating frequency of the quartz resonator. By measuring and calculating this signal with the oscillating circuit unit and analyzing device shown in FIG. 2, the porphyrin concentration can be detected with high sensitivity.

The reason is not clear at present, however it is conceived that attributable are formation of a coagulation block of the latex beads through porphyrin bond and physical adsorption of the latex beads gathering nearby the electrode onto the electrode.

According to the detection method of the present invention, detection of a low molecular weight compound in a solution which has heretofore been considered difficult can be achieved in a way with a highly enhanced sensitivity.

This specification includes part or all of the contents as disclosed in the specification of Japanese Patent Application No. 2000-261373 which is the base of the priority claim of the present application.

Figure 1:
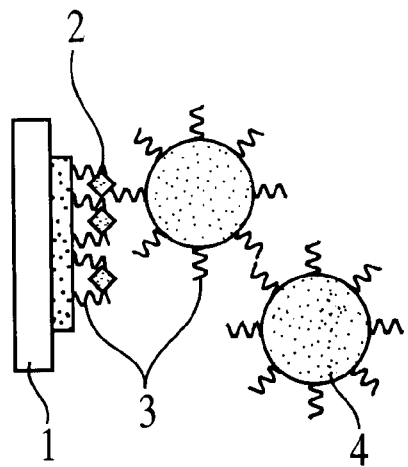
FIG. 1 is a drawing explaining the capture of a compound to be detected according to the detection method of the present invention.
Figure 2:
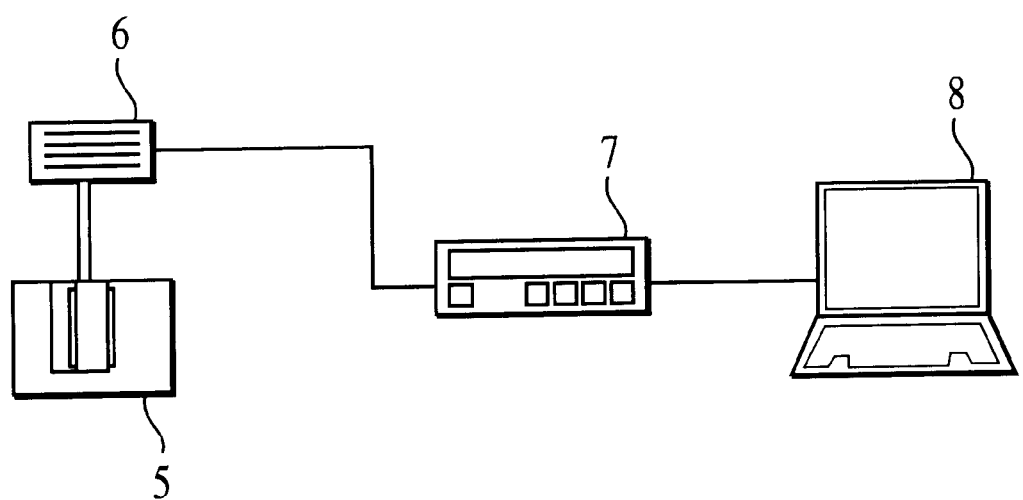
FIG. 2 is a schematic drawing of a detection apparatus preferably used in embodying the method of the present invention.

Each numeral in FIG. 1 and FIG. 2 means the following.

1—quartz resonator

2—porphyrin

3—peptide

4—latex beads

5—measuring vessel

6—oscillating circuit unit

7—frequency counter

8—data analyzing computer

Figure 3:
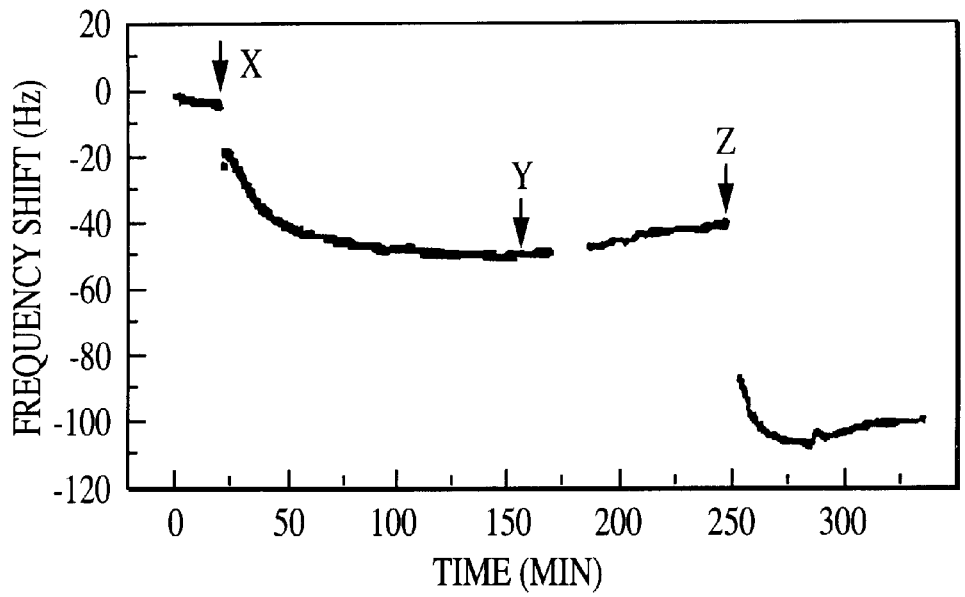

FIG. 3 is a drawing showing fixation of a peptide film onto the surface of a quartz resonator and measurement of the frequency.

Each symbol in FIG. 3 means the following.

X—addition of peptide solution (1 mg/ml)

Y—washing

Z—addition of porphyrin solution (123 μg/ml)

Figure 4:
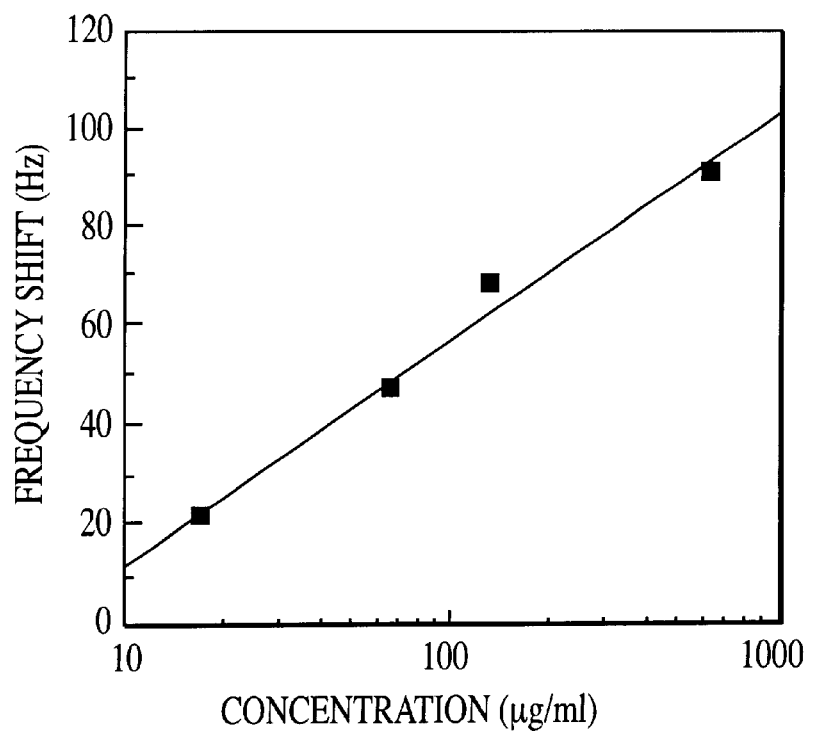

FIG. 4 is a graph showing a relation between porphyrin concentrations and frequency shifts of the quartz resonator in the method of Comparative Example.

Figure 5:
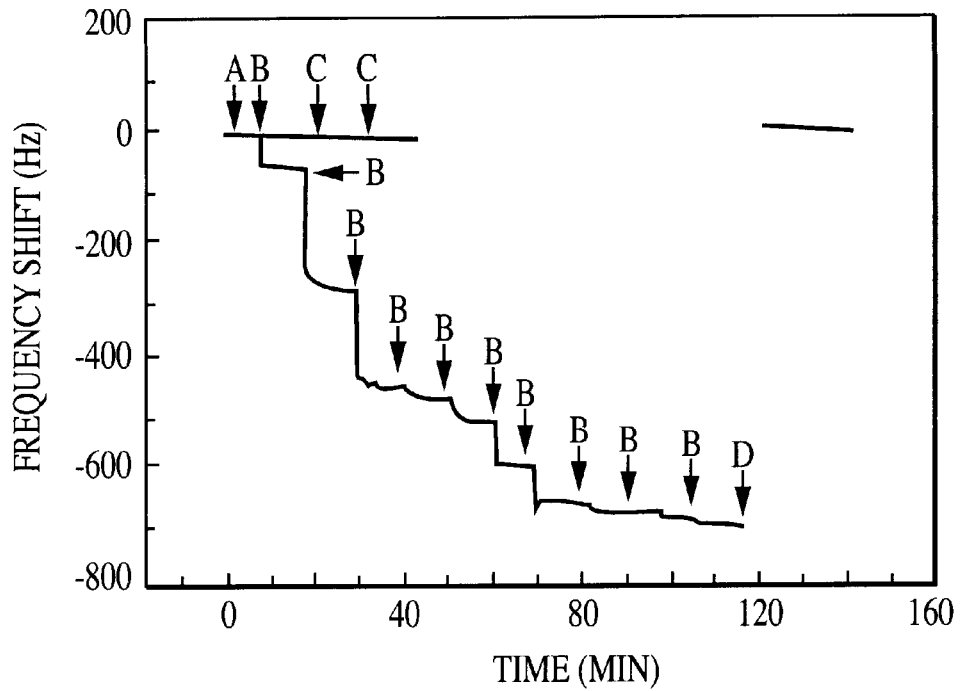

FIG. 5 is a graph showing frequency shifts of the quartz resonator in the case of adding the peptide film-fixated latex beads.

Each symbol in FIG. 5 means the following.

A—addition of porphyrin solution

B—latex beads

C—washing

D—addition of peptide-unfixated latex beads

Figure 6:
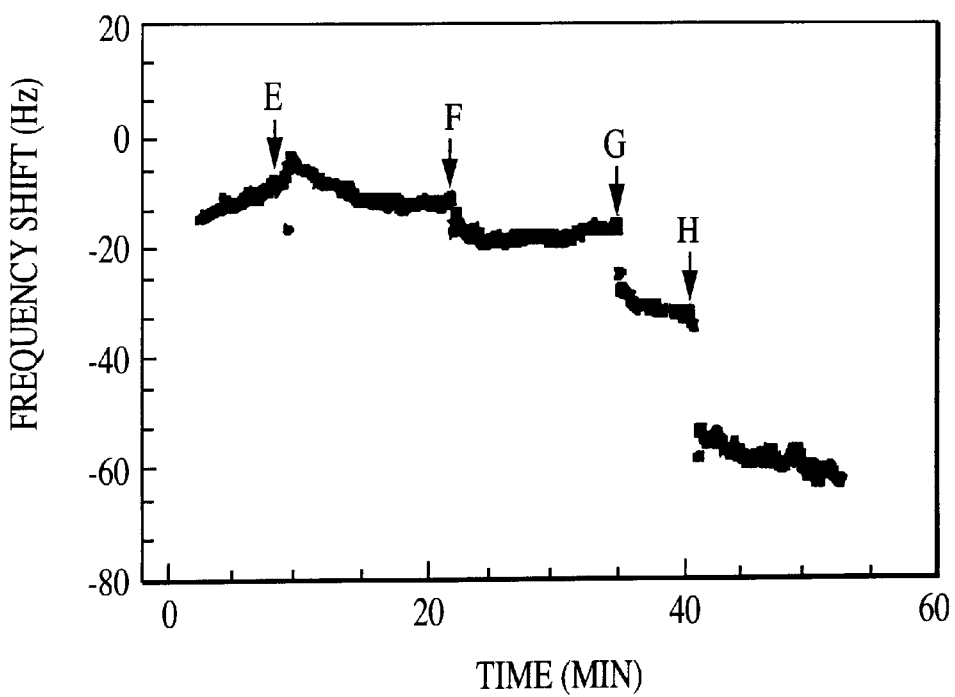

FIG. 6 is a graph showing frequency shifts of the quartz resonator in the case where the peptide film-fixated latex beads are added in various amounts to the low concentration porphyrin.

Each symbol in FIG. 6 means the following.

E—porphyrin (10 ng/ml)

F—latex beads (0.1 µg/ml)

G—latex beads (0.5 µg/ml)

H—latex beads (1 µg/ml)

DETAILED DESCRIPTION OF THE PREFERRED EMBODIMENTS

Hereinafter, the present invention is explained in detail by way of Examples.

REFERENCE EXAMPLE 1

(1) Preparation of Material and Apparatus

[Low Molecular Weight Chemical Substance to be Detected and Film (A)]

As the low molecular weight chemical substance to be detected, porphyrin($H_2$TMpyP; Dojin Kagaku) was used. As the film (A) to be combined with this, there was used a peptide having a sequence of $NH_2$-HisAlaSerTyrSerCys-COOH which was obtained by adding cysteine to $NH_2$-HisAlaSerTyrSer-COOH (Chem. Commun. (1999) 1765) (hereinafter referred to as PSP2).

[Latex Beads]

As the latex beads, styrene-acrylamide copolymer latex beads having a particle size of about 250 nm were synthesized and the amino groups were substituted by carboxyl groups by the surface modification with sodium hydroxide and the resulting beads were used. The specific surface area thereof was 23.6 $m^2$/g and the surface density of charge was −0.45 $C/m^2$.

[Fixation of Peptide Film on Surface of Latex Beads]

Every treatment of beads mentioned below was performed in a concentration of 1 mg/ml with respect to the beads.

The fixation of an oligopeptide film to the latex beads was conducted by thiol coupling. The latex beads were suspended in an aqueous solution containing 5 mM of N-ethyl-N'-(dimethylaminopropyl)carbodiimide and 20 mM of N-hydroxysuccinimide, and the carboxyl groups on the beads were activated for 30 minutes. Washing was conducted twice with 0.1 M borate buffer (pH 8.5). Then the beads were suspended at a concentration of 1 mg/ml in the same buffer containing 10 mM of 2-(2-pyridinyldithio)ethaneamine (PDEA) and stood still for 1 hour to introduce disulfide. Washing was conducted twice with 0.1 M acetate buffer (pH 5.0). The beads were suspended in the same buffer containing 1.5 mM of the peptide PSP2 and shaken for 7 hours to effect fixation of the peptide. Washing was done twice using 0.1 M formate buffer (pH 4.3). Using the same buffer containing 5 mM of cysteine and 1 M of NaCl, there was conducted blocking for the unreacted disulfide. After washing of two times with distilled water, the peptide-fixated latex beads were obtained.

(2) Quartz Resonator Analyzing Device

The quartz resonator used was a square-shaped one of the gold electrode model QA-A9M-AU (made by Seiko EG&G). This resonator has a resonance frequency of 9 MHz in AT-cut. The used oscillating circuit and analyzing device of the quartz resonator was a QCA917 model (made by Seiko EG&G). Because of the measurement in an aqueous solution, one side of the electrode was bonded (covered) with a bare resonator plate having the same specification with a silicone adhesive and rendered for use. An increase in mass that occurs because a substance combines to the surface of the quartz resonator is detected as a decrease in frequency. In the quartz resonator of 9 MHz, adsorption of 1 ng of a substance is detected as a decrease in frequency of about 1 Hz. The constitution of the apparatus is shown in FIG. 2.

(3) Fixation of Peptide on Gold Electrode of Quartz Resonator

The surface of the gold electrode of the quartz resonator was washed and cleansed with a solution of sulfuric acid-hydroperoxide (3:1). The quartz resonator was dipped in 1 ml of apeptide solution for 3 hours for a peptide self-assembled monolayer film to be formed. The peptide solution was prepared from PSP2 using PBS buffer (8 mg/ml NaCl, 9.5 mM phosphate buffer (pH 7.4)) so as for PSP2 to make a final concentration of 1 mg/ml. The peptide solution of 1 ml was put to a 2 ml-volume tube type cell, and therein vertically placed was the quartz resonator on which the peptide was fixated (FIG. 2). The formation of the peptide self-aggregation film was measured with the lapse of time by measurement of the frequency shift (FIG. 3). At the point where the frequency shift became stable washing was carried out with the PBS buffer. The peptide self-aggregation film was stable, and no remarkable falling-off was perceived. As a result, the frequency shift was about 48 Hz, and 48 ng (72 pmol) of the peptide could be fixated on the gold electrode (20 $mm^2$).

COMPARATIVE EXAMPLE

[Measurement of Porphyrin Concentration (Without Use of Latex Beads)]

The PBS buffer (1 ml) was put into a 2 ml tube type cell shown in FIG. 2, and therein the peptide-fixated quartz resonator mentioned above was placed vertically. After waiting until the frequency was stabilized, porphyrin solutions having various concentrations were added, and frequency shifts were measured after waiting until the frequency decrease was stabilized. FIG. 3 shows the frequency shift in the porphyrin solution having a final concentration of 123 µg/ml. FIG. 4 shows a calibration curve summarizing the results of the measurement. When the latex (beads) solution was not added, the frequency decrease which indicated the direct bonding of porphyrin was approximately 10 Hz at a porphyrin concentration of 17 µg/ml, and the detection limit was judged as approximately 20 µg/ml.

EXAMPLE

[Measurement of Porphyrin Concentration (With Use of Peptide-fixated Latex Beads)]

To the porphyrin concentration of 100 ng/ml, each 10 µl of the peptide-fixated latex beads solution (500 µg/ml) was added successively. The results are shown in FIG. 5. It is learned that the frequency shift becomes larger with the addition of the latex beads. Further, it is seen that, though certainly latexbeads, if such latexbeads are used whose surfaces are not fixated with the peptide, the sensitivity is not improved at all.

FIG. 6 shows that, in the case of using the peptide-fixated latex beads having a final concentration of 1 µg/ml, the frequency shift is about 40 Hz to 10 ng/ml porphyrin. On the other hand, in the case of Comparative Example, what responds to the shift of about 40 Hz is 40 µg/ml porphyrin. Therefore, according to the method of Example, it is possible to enhance the detection sensitivity for porphyrin to 1000 times or more compared with the method of Comparative Example.

All the publications, patents and patent applications cited herein are incorporated herein by reference in their entirety.

What is claimed is:

1. A method for detecting a low molecular weight compound in a solution which utilizes a quartz resonator and which comprises capturing the low molecular weight compound between an adsorptive film (A) for a low molecular weight compound provided on a surface of the quartz resonator and an adsorptive film (A) for a low molecular weight compound provided on a surface of a signal enhancing material and comprises detecting a shift in frequency of the quartz resonator before and after the capture.

2. A detection method according to claim 1, wherein one molecule of the low molecular weight compound to be detected is combined to at least one molecule of a material for forming the adsorptive film on the surface of the quartz resonator and at least one molecule of a material for forming the adsorptive film on the surface of the signal enhancing material.

3. A detection method according to claim 1, wherein the adsorptive film (A) for a low molecular weight compound is formed from a peptide.

4. A detection method according to claim 3, wherein the peptide is an oligopeptide.

5. A detection method according to claim 4, wherein the oligopeptide is one obtained by a combinatorial chemical technique.

6. A detection method according to claim 1, wherein the signal enhancing material is synthetic resin beads.

7. A detection method according to claim 6, wherein the synthetic resin beads are polystyrene type beads.

* * * * *